United States Patent [19]

Wang

[11] Patent Number: 4,788,298

[45] Date of Patent: Nov. 29, 1988

[54] PROCESS FOR THE PREPARATION OF COUMARIN COMPOUNDS

[75] Inventor: Richard H. S. Wang, Kingsport, Tenn.

[73] Assignee: Eastman Kodak Company, Rochester, N.Y.

[21] Appl. No.: 693,489

[22] Filed: Jan. 22, 1985

[51] Int. Cl.[4] .................................. C07D 311/16
[52] U.S. Cl. .................................................. 549/289
[58] Field of Search ......................................... 549/289

[56] References Cited

U.S. PATENT DOCUMENTS 3,923,836  12/1975  Bender et al. ................. 549/289
4,452,811  6/1984   della Valle ..................... 549/289

OTHER PUBLICATIONS

Israelstam et al.—Chemistry and Industry—Nov. 1, 1958, 1430.
Shamshurin et al.—Chem. Abst. 64:8127c.
Yang et al.—Chem. Abst. 95:161,758e.
Merchant et al.—Chem. Abst. 86:171,196y.
Zagorevskii et al.—Chem. Abst. 76:140,425m.
Chandhari Chemistry and Industry, Jul. 18, 1983, p. 568.
Mueller et al., Chem. Abst. 91:39255v.
Kozlova et al., Chem. Abst. 75:76528x.

*Primary Examiner*—Jane T. Fan
*Attorney, Agent, or Firm*—J. Frederick Thomsen; William P. Heath, Jr.

[57] ABSTRACT

Disclosed is a three-step process for the preparation of 3-chloro-4-alkyl-7-hydroxy or alkoxycoumarin compounds starting with resorcinol or a monoalkyl ester of resorcinol and chlorinating an intermediate compound with sulfuryl chloride in the presence of acetic acid or an alkyl acetate.

2 Claims, No Drawings

PROCESS FOR THE PREPARATION OF COUMARIN COMPOUNDS

DESCRIPTION

This invention relates to a novel process for the preparation of certain coumarin compounds. More particularly, this invention comprises the preparation of 7-alkoxy-4-alkyl-3-chlorocoumarine and 4-alkyl-3-chloro-7-hydroxycoumarins by first reacting 3-chloro-7-alkoxy-4-alkylcoumarins and resorcinol or a monoalkyl ether of resorcinol with a β-keto ester in the presence of an inert organic solvent and a protonic acid condensation catalyst and treating the intermediate compound thus obtained with sulfuryl chloride in the presence of acetic acid or an alkyl acetate.

Known procedures for preparing the above-described coumarins employ two distinct and separate operations wherein a β-ketoester such as an acetoacetic acid ester is selectively chlorinated to produce an α-chloro-β-ketoester which is then condensed with a resorcinol compound in concentrated sulfuric acid. Such a procedure requires that the intermediate α-chloro-β-ketoester be separated prior to its condensation with the resorcinol compound. Furthermore, the condensation reaction is carried out in a reaction medium of concentrated sulfuric acid in which the product is soluble. Thus, recovery of the product requires dilution of the reaction mixture with large volumes of water which limits the size or amount of product which can be obtained from each manufacturing batch.

In accordance with my invention the aforesaid coumarin compounds may be prepared from a β-ketoester and a resorcinol compound using a single reactor (one pot process). Furthermore, the condensation reaction involved in my process does not require the use of substantial quantities of sulfuric acid which greatly simplifies product recovery. Overall, my process is advantageously efficient and economical due to lower capital, labor and material costs.

This invention provides a process for the preparation of coumarin compounds having the structure

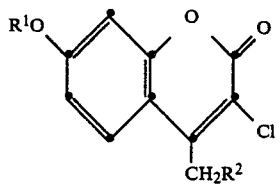

which comprises (1) reacting a resorcinol compound having the structure

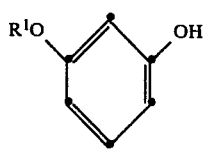

with a β-ketoester having the structure

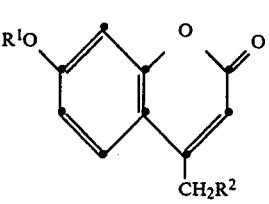

at elevated temperature in the presence of a catalytic amount of a protonic acid condensation catalyst and an inert organic solvent while distilling off reaction by-products to form an intermediate having the structure (2) forming a mixture of acetic acid or an alkyl acetate with the reaction mixture obtained from (1); and (3) adding sulfuryl chloride to the mixture obtained from (2) and heating the resulting mixture; wherein $R^1$ is hydrogen or alkyl of about 1 to 8 carbon atoms such as methyl, ethyl, propyl, butyl, isobutyl, amyl, hexyl, 2-ethylhexyl, octyl, etc.;

$R^2$ is hydrogen, alkyl of about 1 to 6 carbon atoms, chlorine, bromine or an aryl radical such as phenyl and phenyl substituted with alkyl of 1 to 4 carbon atoms, alkoxy of 1 to 4 carbon atoms, chlorine, bromine, etc.; and $R^3$ is alkyl of about 1 to 6 carbon atoms.

The condensation reaction of step (1) normally is carried out at temperatures in the range of about 100 to 160° C. with a range of about 120 to 140° C. being preferred. Pressures moderately below and above atmospheric pressure can be used if desired, e.g., to control the volatility of the reactants and reaction by-products. However, the process normally is carried out at atmospheric pressure or pressures slightly above atmospheric such as those generated in the reactor in which the process is carried out.

The protonic acid condensation catalysts useful in the condensation reaction are well known in the art. See, for example, Chemistry and Industry, July 18, 1983, page 568. Such catalysts are moderate to strong acids and include sulfuric acids, phosphoric acids such as polyphosphoric acid and sulfonic acids such as methanesulfonic acid, benzenesulfonic acid and toluene-sulfonic acid. The amount of condensation catalyst can be varied substantially depending on other process variables such as the particular reactants, solvent temperatures, and catalyst employed. Amounts in the range of about 0.1 to 5.0 mole percent based on reactant (I) will give satisfactory results although amounts in the range of about 0.5 to 2.0 mole percent are preferred.

The organic solvents suitable for use in the condensation step should be inert relative to the reactants and catalyst employed and be capable of being vaporized at the temperature at which the condensation reaction is carried out as a component of a constant boiling mixture with one or both of the reaction by-products (water and $R^3OH$). Examples of suitable solvents include hydrocarbons such as heptane and octane and chlorinated hydrocarbons such as chlorobenzene and dichlorobenzene. The amount of solvent used typically is about 0.5 to 3 times the weight of the reactants.

The reactants used in the condensation reaction are known compounds available from various sources and/or can be prepared according to known procedures. Although the mole ratio of the reactants can be varied considerably, the process can be carried out most economically with approximately equimolar amounts of each.

At the conclusion of step (1) the resulting reaction mixture should be essentially free of the by-products of the condensation reaction. Thus, the by-products, as in typical condensation reactions, may be removed during the reaction by vaporizing them separately or as an azeotrope with the inert, organic solvent.

In the second step of my novel process the mixture, comprising an intermediate coumarin, catalyst, residual solvent and some unreacted material, resulting from step (1) is combined with acetic acid or a $C_1$–$C_4$ ester of acetic acid, preferably methyl or ethyl acetate. While the step (1) mixture may be added to the acetic acid or ester, the process is most efficient and economical if the acetic acid or ester is added to the reactor in which the condensation step was carried out and in which contains the mixture resulting from step (1).

The amount of sulfuryl chloride added to the mixture obtained from step (2) normally will be equimolar to the amount of intermediate courmarin present although up to a 20 percent mole excess may be used. When approximately equimolar amounts of reactants are used in step (1) the mole ratio of compound (I) to sulfuryl chloride usually will be in the range of about 1.0 to 1.2. The sulfuryl chloride may be added continuously or intermittently over a period of time so that the addition rate gives selective chlorination of the intermediate coumarin.

The temperature at which the third step is carried out can be varied substantially although too low of temperatures result in a slow chlorination rate and possibly decreased selectivity of chlorination. Exccessively high temperatures cause the sulfuryl chloride to decompose at a rapid rate with loss of the decomposition products resulting in incomplete chlorination. Temperatures in the range of about 40 to 100° C. can be used depending on the particular chlorination solvent employed. The chlorination reaction preferably is conducted at temperatures in the range of about 60°–80° C.

The process of the invention is particularly useful for the preparation of 3-chloro-7-hydroxy-4-methylcoumarin, a compound used in the preparation of coumaphos, a fungicide and bactericide used on livestock.

The process is further illustrated by the following example.

EXAMPLE 1

A mixture of resorcinol (11.0 g; 0.1 mol), methyl acetoacetate (13.9 g; 0.12 mol), sulfuric acid (0.1 g) and octane (40 ml) was heated to reflux for five minutes at about 100° C. (pot) and 75° C. (head). After 18.5 ml of distillate were removed slowly and continuously over a period of 20 minutes, the pot temperature rose to 120°-5° C. The reaction mixture was heated at 120°-5° C. for one hour and then cooled to 60° C. Acetic acid (200 ml) was added and the mixture was heated to 75° C. Sulfuryl chloride (15 g; 0.11 mol) was added slowly to the mixture at below 85° C. over a period of 11 minutes. The resulting mixture was heated at 75°-80° C. for two hours and then acetic acid (160 to 180 ml) was distilled off under reduced pressure at a temperature below 100° C. The viscous reaction mixture was cooled to room temperature and 200 ml water was added with vigorous stirring. After cooling to 10°-15° C. the reaction mixture was filtered and the product was washed with water and dried. The yield of crude product (20.7 g) was 98% based on the resorcinol used. The product assayed 88% 3-chloro-7-hydroxy-4-methylcoumarin by G. C. analysis.

The invention has been described in detail with particular reference to preferred embodiments thereof, but it will be understood that variations and modification can be effected within the spirit and scope of the invention.

I claim:

1. Process for the preparation of a coumarin compound having the formula

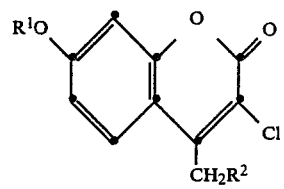

which comprises
(1) reacting a resorcinol compound having the structure

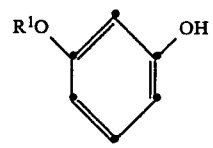

with a β-ketoester having the structure

at elevated temperature in the presence of a catalytic amount of a protonic acid condensation catalyst and an inert solvent while distilling off reaction by-products to form an intermediate having the structure

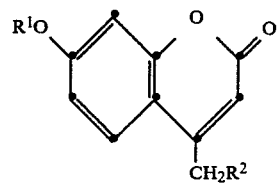

(2) forming a mixture of acetic acid or an alkyl acetate with the reaction mixture obtained from (1); and
(3) adding sulfuryl chloride to the mixture obtained from (2) and heating the resulting mixture;
wherein
$R^1$ is hydrogen or alkyl of about 1 to 8 carbon atoms;
$R^2$ is hydrogen or alkyl of about 1 to 6 carbon atoms, chlorine, bromine or an aryl radical; and
$R^3$ is alkyl of about 1 to 6 carbon atoms.

2. Process according to claim 1 for the preparation of 3-chloro-7-hydroxy-4-methylcoumarin which comprises
 (1) reacting resorcinol with an alkyl acetoacetate in the presence of a catalytic amount of a protonic acid condensation catalyst and an inert solvent while distilling off reaction by-products to form 7-hydroxy-4-methylcoumarin;
 (2) forming a mixture of acetic acid or an alkyl acetate with the reaction mixture obtained from (1); and
 (3) adding sulfuryl chloride to the mixture obtained from (2) and heating the resulting mixture.

* * * * *